United States Patent [19]

Kasper et al.

[11] Patent Number: 4,794,086
[45] Date of Patent: Dec. 27, 1988

[54] METHOD FOR MEASUREMENT OF IMPURITIES IN LIQUIDS

[75] Inventors: Gerhard Kasper, Downers Grove; Horng Y. Wen, Brookfield, both of Ill.

[73] Assignee: Liquid Air Corporation, Walnut Creek, Calif.

[21] Appl. No.: 801,305

[22] Filed: Nov. 25, 1985

[51] Int. Cl.$^4$ .......................... G01N 1/28; G01N 15/02
[52] U.S. Cl. ...................................... 436/36; 73/61 R; 356/36; 356/37; 356/335; 356/336; 436/164; 436/181
[58] Field of Search ........................ 356/36, 37, 72, 73, 356/335–343; 73/29, 28.61 R; 436/181, 36, 164

[56] References Cited

U.S. PATENT DOCUMENTS

| | | | |
|---|---|---|---|
| 3,765,771 | 10/1973 | Shaw | 356/103 |
| 3,854,321 | 12/1974 | Dahneke | 356/336 X |
| 4,173,415 | 11/1979 | Wyatt | 356/336 |
| 4,284,496 | 8/1981 | Newton | 356/72 X |
| 4,361,400 | 11/1982 | Gray et al. | |
| 4,519,983 | 5/1985 | Espitalie et al. | 436/155 X |

FOREIGN PATENT DOCUMENTS 0192259 9/1985 Japan .

OTHER PUBLICATIONS

Salkowski et al., *Surface Contamination:Proceedings of a Symposium Held at Gatlinberg, Tenn., Jun. 1964,* Edited By B. R. Fish, Published by Pergamon Press, New York, 1964, pp. 209-218.
TSI, Incorporated, "Vibrating Orifice Aerosol Generator" product brochure, 1983, 6 pages.
TSI, Incorporated, "Particle Counting, Condensation Nucleus Counter Model 3020" product Brochure, 2 pages.
TSI, Incorporated, "Electrostatic Classifier Model 3071" product brochure, 4 pages.
TSI, Incorporated, "The APS 33 Aerodynamic Particle Sizer" product brochure, 6 pages.
Particle Measuring Systems, Inc., "Laser Aerosol Spectrometer System, Model LAS-X" product brochure, Jun. 1982, 2 pages.
Mercer, Aerosol Technology in Hazard Evaluation, Published by Acedemic Press, New York, 1973, pp. 336-367.
Liu, J. of Air Pollution Control Association, vol. 24, No. 12, pp. 1070-1072, 1974.
Campbell et al., Anal. Chem., vol. 50, No. 7, pp. 963-964, 1978.
"Standard Test Method for Nonvolatile Matter in Volatile Solvents for Use in Paint, Varnish, Lacquer, and Related Products", American Society for Testing and Materials (ASTM), D1353-83, pp. 1-2, 1983.
"Determination After Evaporation", Book of Semi Standards, vol. 1, Chemical Division, 1978, pp. 6-7.
Sem; Electrical Aerosol Analyzer: Operation, Maintenance, and Application; Aerosol Measurement, Univ. Fla. 1979, pp. 400-429.
Pui et al.; Electrical Aerosol Analyzer: Calbration and Performance; Aerosol Measurement; Univ. Fla. 1979, pp. 384-399.
Rimberg; Counting Efficiencies of Three Single Particle Aerosol Counters; Aerosol Measurement; Univ. Fla. 1979, pp. 321-336.

*Primary Examiner*—Barry S. Richman
*Assistant Examiner*—Robert J. Hill, Jr.
*Attorney, Agent, or Firm*—George F. Bethel; Patience K. Bethel

[57] ABSTRACT

Method and apparatus for the measurement of sub-ppm concentrations of impurities in liquids. The liquid to be measured for impurities is dispersed into uniform droplets of a precisely known diameter D in a gas stream, such as air, using for example, a vibratory orifice generator. The dispersed droplets evaporate in the gas stream to leave a residue particle having a diameter d, which can be measured for example by means of a laser light scattering spectrometer. The concentration by volume, $C_v$, of the impurities can then be calculated according to the equation; $C_v = (d/D)^3$.

11 Claims, 3 Drawing Sheets

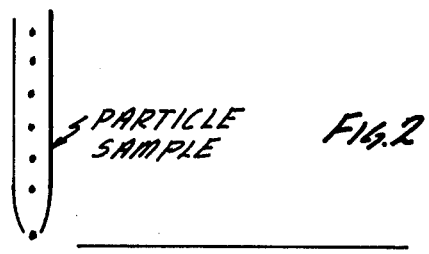
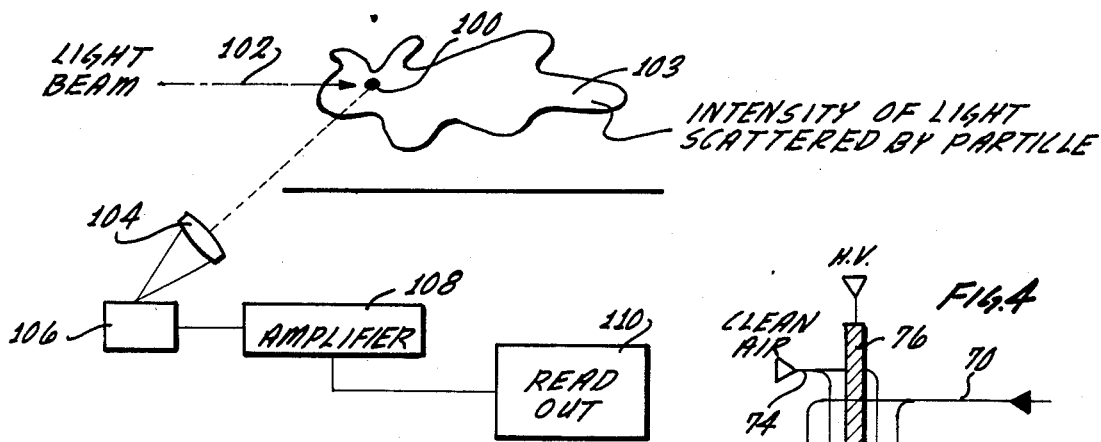
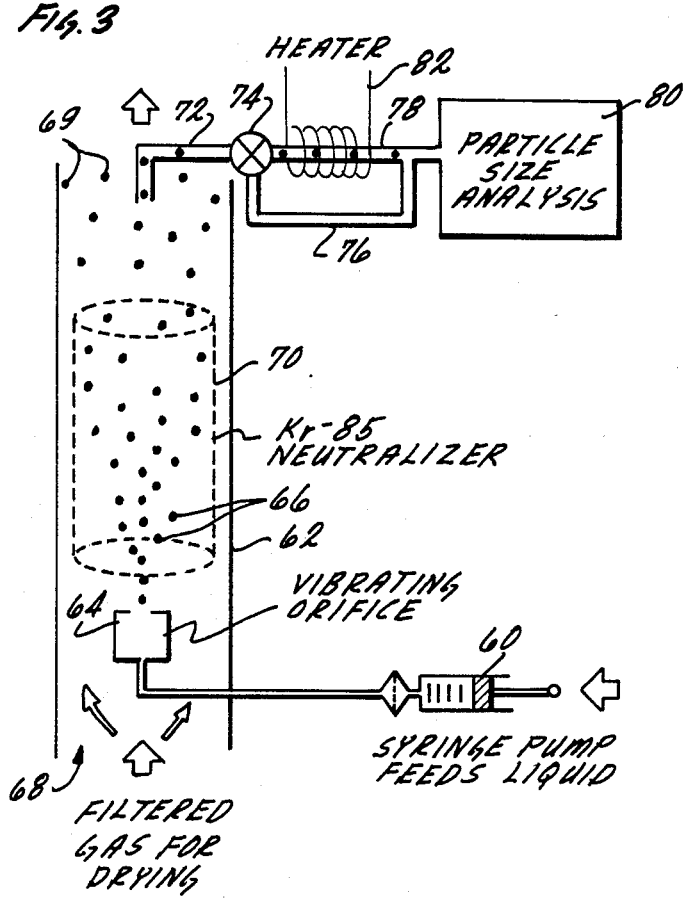
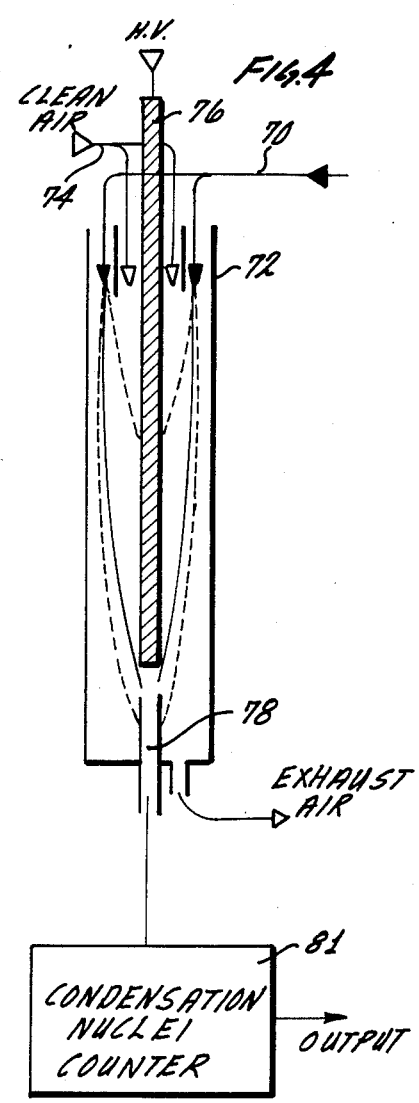

4,794,086

METHOD FOR MEASUREMENT OF IMPURITIES IN LIQUIDS

BACKGROUND OF THE INVENTION

This invention relates to the measurement of impurities in liquids as, for example, between 0.01 ppm to $10^4$ ppm, and especially to a method for the rapid measurement of impurities in ultrapure liquids containing sub-ppm concentrations of impurities.

DESCRIPTION OF THE PRIOR ART

It has been found in recent years that ultrapure water is essential to the research, development and production of semiconductor devices. The amount of water required can amount to as much as 2 to 5 liters for a single "chip" produced. The standards set by the semi-conductor industry require sub-ppm amounts of contaminants in the water. These requirements for ultrapure water have also increased the need for methods for measuring the concentration of trace contaminants in the water.

Problems associated with measurements of such contaminants are complicated by the fact that ultrapure water is capable of attacking almost all materials of construction. Thus, any materials in contact with the pure water will rapidly dissolve and change the condition thereof. As a consequence, it becomes even more important to be able to rapidly measure the amount of contaminants within such water so that such contaminants can be held to acceptable limits. Similar requirements are necessary for other liquids which are needed in the ultrapure state.

At the present time, the standard test method used to detect impurities in liquids measures the residue remaining after evaporation of a volatile liquid and heating of the dish and residue at 105° C. for 30 minutes. The Residue after Evaporation test method is laid down in the BOOK OF SEMI STANDARDS 1985, Volume 1, Chemicals Divisions, p. 6, section 3.3, Determination of Residue After Evaporation; in the Annual Book of ASTM Standards, 1984, Designation: D 1353-83, Standard Test Method for Nonvolatile Matter in Volatile Solvents for use in Paint, Varnish, Lacquer, and related products; as well as in Analytical Chemistry, Volume 50 No. 7, June 1978 issue, in the article entitled "Analysis of High Purity Chemicals: Examination and Improvement of the Residue After Evaporation Test for Solvents", by Campbell and Hallquist.

The test methods are basically the same. The last method, for example, includes cutting a circle of "household type" aluminum foil having a thickness of 0.006 cm and about 20 cm in diameter. After washing with the liquid to be measured for impurities and air drying, the foil is pressed around the bottom of an 800 ml beaker. The resulting aluminum foil dish is then heated at 105° C. for thirty minutes. In cases where the liquid used attacks aluminum, a platinum dish is used. The dish is then cooled in a desiccator charged with calcium chloride for about 30 to 45 minutes.

Static electricity is then discharged with a radioactive source and the dish is then weighed. Next, the dish is placed into a Thiers assembly having nitrogen flowing into it which has been filtered through a 0.8 um membrane filter. An amount of the liquid to be measured which is equivalent to 200 grams is added to the dish. The dish and liquid are then exposed to a heat lamp placed above it and to a low temperature hot plate below. The heating is adjusted so that evaporation takes place at not more than 8 ml/min.

After evaporation of the liquid, the dish still in the Thiers assembly is placed in an oven at 105° C. for 30 minutes, followed by cooling in the same desiccator mentioned above. After about 35 to 45 minutes the static electricity is discharged and the resulting dish is then weighed. The weight of the residue can be determined by subtracting the original weight of the dish alone.

The accuracy of the above described method permits the detection of residues as low as 0.4 ppm. Possibility of error can originate from atmospheric contamination, contamination from the apparatus, loss of residue if transferred, cooling time of the dish before weighing, moisture pick-up from the air, and loss of residue through entrainment in escaping vapor.

It will be apparent from the above description that the above method while fairly accurate, requires extended time periods for analysis of impurities and thus does not fulfill the need for a rapid method for the measurement of impurities in liquids.

The present invention addresses the needs of the semiconductor industry, as well as other industries requiring the rapid analysis of liquids for impurities contained therein. The method is extremely accurate, faster, and more economical with regard to the small amount of liquid required than the standard method. The basic requirements are that the liquid to be analyzed must be capable of being dispersed into droplets, be capable of evaporation, and be of a nature which can be contained in an appropriate vessel without reacting or dissolving its walls to add additional impurities.

SUMMARY OF THE INVENTION

The method of the invention includes dispersing the liquid to be measured for impurities into uniform droplets of a precisely known diameter D in a gas stream under ambient conditions. The droplets are then evaporated rapidly to leave a residue particle having an unknown diameter d. Any static charge on the droplets and/or residue particles is then neutralized and the diameter d of the residue particles is then measured. The residue concentration by volume, $C_v$, within the liquid can then be calculated according to the equation:

$$C_v = (d/D)^3$$

The liquid to be dispersed is dispersed preferably by means of a vibrating orifice generator wherein a liquid jet fed by a syringe pump is broken up in a controlled manner into highly uniform droplets by means of a piezoelectric vibrator. The vibrator vibrates at a selectable frequency which controls the uniform size of the droplets. As soon as the droplets are formed they are introduced into a turbulent gas flow such as air or nitrogen to disperse the droplets and rapidly dry them, each droplet leaving behind the residue particle. Neutralization of any static charge can be effected by use of a Krypton-85 radioactive neutralizer.

According to one embodiment of the invention, the gas stream of residue particles can be periodically passed through a heated zone to cause evaporation of organic impurities. This permits a determination of whether the residue particle is organic or inorganic. By comparing the size of the particle prior to exposure to heat with that of the size of the particle after exposure to heat, the amount of organic impurities can be determined.

The residue particles issuing from the droplet generator each have a diameter d which is measured according to the invention method. For this purpose, use can be made of any particle sizing device, such as a light scattering spectrometer. Other devices which can be used are described in the detailed description of the invention which follows.

Knowledge of the diameter D of the droplet and the diameter d of its residue particle enables calculation of the concentration by volume, $C_v$, of the impurity in the liquid by the equation:

$$C_v = (d/D)^3$$

The invention will be more readily understood by reference to the attached drawings.

BRIEF DESCRIPTION OF THE DRAWINGS

FIG. 2 shows a general schematic diagram of a light scattering particle spectrometer;

FIG. 3 shows a schematic diagram of the process of the invention with emphasis on the droplet generator;

FIG. 4 shows a schematic flow diagram of the invention process using an electrostatic classifier and a condensation nuclei counter.

DETAILED DESCRIPTION OF THE INVENTION

Figure 1:
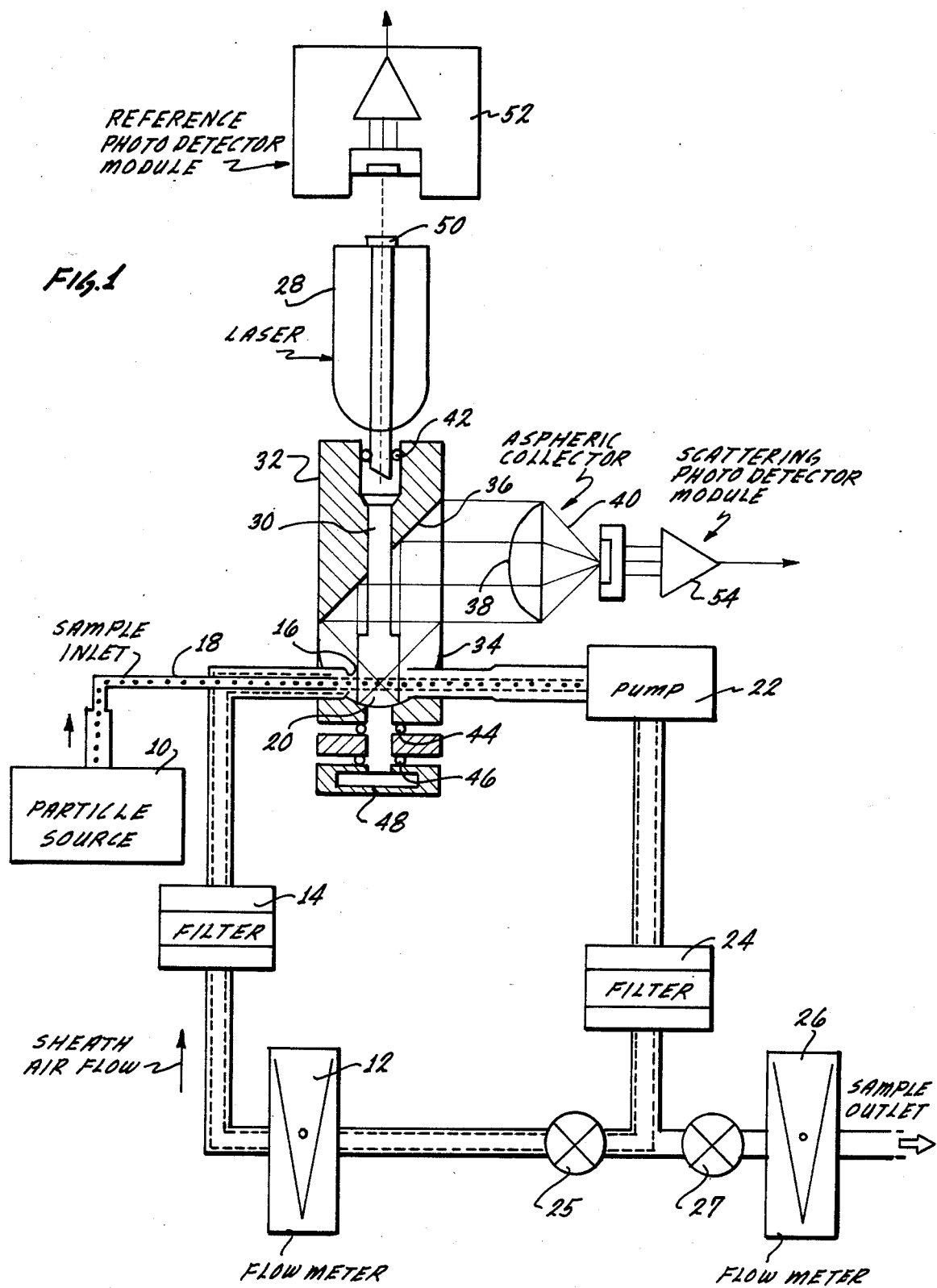
FIG. 1 shows a schematic flow diagram of the method of the invention utilizing a particle source from a droplet generator and a laser light scattering particle spectrometer.

The accuracy of the invention method is dependent on accurate knowledge of the diameter D of a droplet of a liquid to be analyzed for impurities, and the measurement of the diameter d of the residue particle remaining after evaporation of the liquid from the droplet.

A vibrating orifice droplet generator is preferred for monodispersing uniform droplets into a gas stream. A preferred droplet generator is Model 3450 availabe from TSI, Inc. This device is known in the scientific literature. See for example, Berglund, R. N. and Liu, B. Y. H. (1973) Eviron. Sci. Technol. 7, 147.

A schematic of a droplet generator can be seen in FIG. 3. As shown, a syrine pump 60 feeds liquid to be sampled at a preset flow rate into a chamber 62 where a vibrating orifice 64 produces identical, uniform droplets 66 one by one as the stream passes through the vibrating orifice. The vibrating orifice 64 generates uniform droplets 66 by controlling the breakup of the liquid jet. The production of non-uniform droplets is avoided by applying a periodic disturbance of an appropriate frequency in a regulated manner. This process produces highly uniform droplets having a standard deviation typically less than 1% of the median droplet size.

The vibrating orifice 64 is extremely small in size and the liquid solution from the syringe pump 60 is fed at a predetermined rate. A piezoelectric ceramic vibrates the orifice 64 at a constant frequency, which vibration is driven by an oscillating voltage potential. As the uniform droplets 66 are formed, they are introduced into a turbulent air jet 68 which enters the chamber 62 at the bottom. The turbulent air jet 68 acts to disperse the droplet and prevent coagulation. A larger volume of filtered, clean, dry air is also added to the chamber 62 to induce evaporation of the liquid.

As the droplets 66 pass upwardly through the chamber 62, they are exposed to the deionizing effects of a Krypton-85 neutralizer 70 within the chamber to neutralize any static charge on the droplets or residue particles.

As the droplets pass through the neutralizer 70 and the length of the chamber 62, the liquid is evaporated from the droplets 66 to produce residue particles 69 which are composed of organic and/or inorganic components. The particles are drawn into a tube 72 controlled by a valve 74 which directs the particles by way of tube 76 or 78 to a particle size analyzer 80. A portion of the stream can be directed through tube 78 where it is exposed to heater 82. A comparison of the diameter of the particles which have passed through heater 82 with the diameter of those which have passed through tube 76 gives a determination of whether or not the residue particle is organic in nature.

One type of particle size analyzer, a light scattering particle spectrometer, is shown schematically in FIG. 2. As shown, a particle 100 to be measured is made to pass through an incident light beam 102 causing the light to scatter as shown at 103. The light scattered is picked up by a collection optics system 104 which directs the light to a photomultiplier tube or light sensitive diode 106. The signal from the photomultiplier tube or light sensitive diode 106 is directed to an amplifier 108 and then to a read-out device 110.

The device which is preferred for measurements of residue particle diameters in the range of 0.1 um to 12 um is a laser light scattering particle spectrometer available from Particle Measuring Systems, Inc. Model LAS-X or LAS-250X. A schematic of this device is shown in FIG. 1.

A sample droplet generator substantially as shown in FIG. 3 monodisperses a liquid to be measured for impurities into uniform droplets in air, each droplet having a diameter D, which forms after evaporation, a residue particle sample having a diameter d. This output of the droplet generator constitutes the particle source 10 shown in FIG. 1. The residue particle sample stream issuing from particle source 10 is drawn through hypodermic tubing 18 having a 500 um diameter. At the same time sheath air controlled by a flow meter 12 flows through filter 14 and is aerodynamically focused at nozzle 16 where the residue particle sample stream joins the flow of filtered sheath air. The combined flow of filtered sheath air and the residue particle sample stream intersects a laser beam at point 20 before being drawn by pump 22 to filter 24. Filter 24 collects the residue particles while permitting the passage of air which is directed to flow meter 26 and out of the system. Needle valves 25 and 27 control the amounts of air passing in and out of the system.

The laser 28 is a hybrid He-Ne 632.8 nm tube with an aluminum envelope especially designed for the laser. The active laser cavity 30 is contained within a housing 32. The laser 28 is used in conjunction with two front surface mirrors 34 and 36. The first collecting surface mirror is a parabolic mirror 34 through which the particles to be analyzed pass through its focus during the sampling process. The parabolic mirror 34 has been gold-plated to provide 90% reflectivity at 632.8 nm.

The second surface mirror 36 is at a 45° angle and is dielectrically coated to provide greater than 99% reflectivity at 632.8 nm. An aspherical refracting element 38 which is also dielectrically coated is housed in a single aluminum block 40.

The laser cavity 30 is sealed by means of O-rings 42, 44 and 46. Also, at the point diametrically opposite from the laser 28 is an external mirror 48. A sealed mirror 50 is rotated between the laser and a reference photodetector module 52. A scattering photodetector module 54 completes the optical system.

The optical system described above supplies an energy density in excess of 500 W cm$^2$ with a beam width of 400 um–600 um. The combined imaging system has an effective magnification of 4×. The system collects light from 35%–120% providing a 2.2 pi steradian solid angle.

The particle sampling takes place with the aerodynamically focused jet comprised of the particle sample stream from the particle source 10 surrounded by a filtered sheath air flow. The particle sample stream is positioned at the focus of the parabolic mirror 34 at point 20 of FIG. 1. Light collected from the laser is columnated by the parabolic mirror 34 and after reflecting off the 45° flat mirror 36, it is refocused by the aspheric lens 38. The collected light is converted by the photodetector module 54 into a signal photocurrent.

Figure 5:
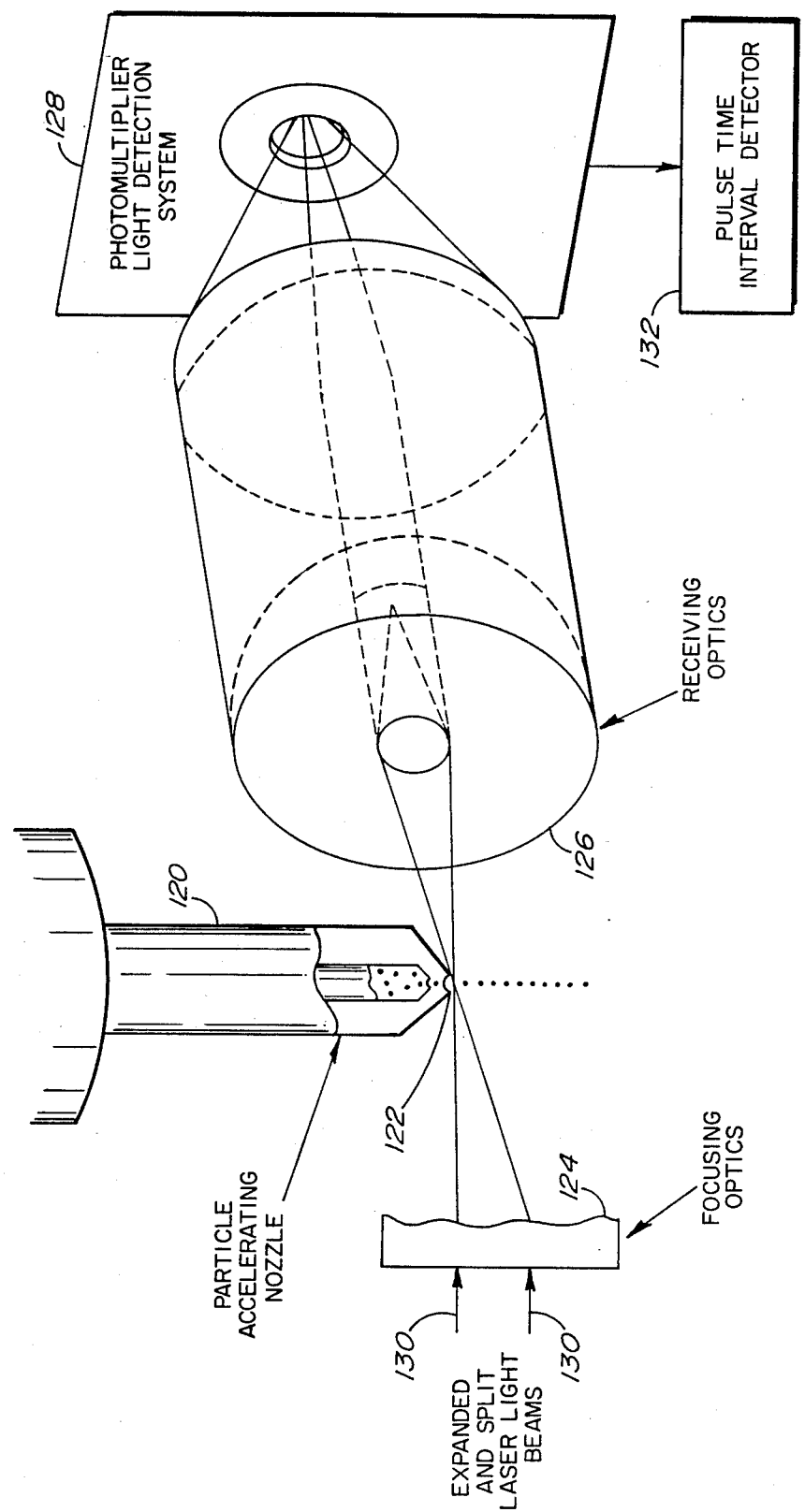
FIG. 5 shows a schematic diagram of an aerodynamic particle sizer.

An alternative device for measuring the diameter of residue particles which is especially suited for residue particles having a diameter d greater than about 0.5 um is an APS 33 aerodynamic particle sizer manufactured by TSI, Incorporated and which is shown schematically in FIG. 5. The principle of the aerodynamic particle sizer is based on the fact that if one can measure the speed of an accelerating particle in a known flow field, one can measure its true aerodynamic size. In this device, particles are drawn through a particle accelerating nozzle 120 to produce a precisely controlled accelerating high-speed jet of air. The velocity of the particle is measured by a laser velocimeter. During the entire measurement period, the velocity at any point in the flow field remains constant within the jet, depending upon the aerodynamic size characteristics of the particle. Small particles will accelerate more rapidly than larger particles.

The particle speed is actually measured at the exit 122 of the particle accelerating nozzle 120. The laser velocimeter system consists of a laser light source (not shown), a beam expander and splitter (not shown), focusing optics 124, receiving optics 126, and a photomultiplier light detection system 128. In operation, an expanded laser beam is split to form two expanded and split laser light beams 130 which are then focused into two parallel planes immediately below the accelerating flow nozzle. Each particle passing through these two parallel planes produces two pulses of scattered light which are collected and focused onto the photomultiplier light detection system to produce two electrical pulses. The time interval between the two pulses is measured by pulse time interval detector 132 and indicates the velocity of the particle and thus its aerodynamic size.

In order to measure the particle diameter of residue particles having a diameter below about 0.1 um to as small as about 0.01 um, use can be made of an electrostatic classifier in conjunction with a particle detector, for example a condensation nuclei counter. An electrostatic classifier of the type described is manufactured by TSI, Inc.

The principle of the electrostatic classifier is illustrated schematically in FIG. 4. The residue particle stream produced by a droplet generator is passed through a Kr-85 bipolar charger to establish a bipolar equilibrium charge level on the particles. Within the diameter size range of about 0.005 um to 0.3 um, most particles obtain a single positive or negative electrical charge unit. The positively and negatively charged particles are then passed into a device substantially as shown in FIG. 4 which is a differential electrical mobility analyzer. This device removes all particles except those within a narrow mobility range, which range depends upon the voltage.

The particles enter the device at inlet 70 where they are carried along by means of a stream of air entering at inlet 74 through the device within a grounded chamber 72, and are placed into contact with a variable high voltage supply source 76. Within the chamber 72 all particles are removed except those within a narrow mobility range depending upon the voltage. As the voltage on the mobility analyzer is adjusted over its operational range, the residue particle exhaust stream of unknown diameter d exits chamber 72 through outlet 78 where it is directed to a condensation nuclei counter 81. When the condensation nuclei counter 81 detects particles, the diameter of the particles can be precisely determined from the knowledge of the mobility analyzer voltage, the constant flow rate, and the system geometry, since all the particles have a single charge.

One type of condensation nuclei counter which can be used is Model 3020 manufactured by TSI, Inc. In this device, butanol is made to condense on submicrometer particles which are passed over the surface of a butanol pool at a temperature of about 33° C. The vapor condenses onto the particles causing them to grow to about 10 um droplets. The particles with the condensed butanol vapor are then passed through a beam of a high intensity and reliable 10,000-hour halogen lamp. The resulting forward light scattering is picked up by a photodetector which produces a photodiode output which has a high signal to noise ratio. The analog output is linearly proportional to the concentration over the entire concentration range.

DESCRIPTION OF THE PROCESS STEPS

The process of the invention provides a means for the rapid measurement of sub-ppm concentrations of impurities in liquids. The method allows the determination of both organic and inorganic impurities.

Ideally, liquids to be measured for impurities should have a relatively low viscosity under ambient conditions which permits the generation of droplets. Also, they should be capable of being contained in an appropriate vessel with which such liquids would be nonreactive in order to avoid the introduction of additional impurities not present in the original liquid. Finally, the liquids should be capable of evaporation.

In order to measure the impurities in the liquid, it must first be dispersed into uniform droplets of a precisely known diameter D in a gas stream. While the drawings illustrate one type of droplet generator, any type of droplet generator can be employed which ultimately produces uniform droplets of a precisely known diameter D. For example, the liquid can be directly monodispersed using a monodisperse aerosol generator of the type described in FIG. 3. A preferred device is Model 3450 available from TSI, Inc.

Generally, in the case of the vibrating orifice generator as shown in the drawings, droplet diameter size can be within the range of 1 um to about 200 um, with preferably a droplet size range of about 20 um to about 50 um. The last range gives excellent results for impurity measurements at the ppm level.

In order to avoid contamination of the liquid during the measuring process, the materials which are contacted by the liquid must be considered in order to achieve the most accurate results. For example, stainless steel is commonly used for the vibrator head and orifice plate in the vibrating orifice generator. Teflon is the material used for tubing, gaskets, a filter, and a 13 mm filter that protects the micro-orifice. Also, polypropylene is the material commonly used in the filter holder. The syringe materials must also be considered. The exact choice of materials will depend on the type of liquid which is being used.

For measurement of impurities in most organic solvents and water, stainless steel and Teflon are preferred. In addition, the polypropylene filter housing does not appear to react with most organic solvents or water. The syringe includes not only the material of which it is made, but also a plunger. Satisfactory results have been obtained with a syringe of borosilicate glass with a Teflon plunger for the case of isopropanol. For water measurements, a polypropylene syringe with a neoprene plunger has given satisfactory results. It should be remembered though, that certain types of materials will react with the liquid to be measured, and each instance should be reviewed for the appropriate choice of materials.

Normally, the gas stream to be used for the generation of the droplets is ultrafiltered air. In other instances, any ultrafiltered gas such as nitrogen or other inert gas can be used as long as the gas is non-reactive with the liquid to be measured or with the impurities present.

Preferably, the droplets are introduced into a turbulent gas flow to encourage the rapid evaporation of the liquid from the impurities to leave a residue particle having a diameter d.

It is important to neutralize any static charge on the droplets or the residue particles. Ideally, the static charge should be reduced to near Boltzman end charge equilibrium. Neutralization of the particles and droplets can take place at the same time that the droplets are being generated or while they are evaporating or drying.

Excellent results have been obtained for neutralization of the static charge on the droplets and residue particles with a Krypton-85 radioactive neutralizer. However, other isotopes can be used as, for example, Am-131.

As shown in FIG. 3, the droplet generator can be equipped with a short heating section near the outlet in order to heat the gas particle stream. The particles can be passed through this section to permit an estimate of whether the residue is of organic or inorganic origin. If the impurity consists of an organic residue, a diameter change will be observable after heating. The difference between the diameter of the particle after passage through the heating section when compared with the diameter of a particle which has not been exposed to the heating section, permits the determination of the organic portion of the impurity by the difference in diameter.

In using the vibrating orifice generator, the volume, V, of each droplet can be calculated from the operating parameters using the formula:

$$V = Q/F$$

where Q is the volume flowrate of liquid in the jet, and F is the excitation frequency of the periodic disturbance. For maximum accuracy, the volume flow rate of the liquid Q needs to be redetermined in each case for each individual syringe.

After V has been determined, the diameter D of the droplet is calculated by solving for D in the formula for the volume of a sphere:

$$V = D^3 \pi / 6$$

$$D = (6V/\pi)^{\frac{1}{3}}$$

and since $V = Q/F$, $$D = (6Q/\pi F)^{\frac{1}{3}}$$

The liquid volume flow rate can be measured by weighing the amount of liquid dispensed by the syringe pump over a given period of time. For example, 10 cm$^3$ can be injected into a small flask sealed with a septum to minimize evaporation. Error analysis has shown only negligible errors for time measurements, weighing and evaporation losses. It was found during a test duration of 64 minutes that evaporation from the open flask amounted to only 0.06 g. Only the last drop which amounted to about 0.05 cm$^3$ or about 0.5% for a liquid feed rate of 0.153 cm$^3$/min. provided the main uncertainty. This resulted in a total uncertainty of less than ±1% in Q.

Measuring the parameters Q and F independently from the readings provided by the vibrating orifice generator provided an overall uncertainty of about $\frac{1}{3}$% for D.

Using a 20 um orifice and a frequency range of 40–80 kHz, the combined uncertainty and stability for F was determined to be about 0.2%.

After the droplets have been generated and are flowing through the drying tube of the vibrating orifice generator, there is produced a dilute gas stream of dried residue particles which are particles from which the liquid has evaporated as much as possible under ambient conditions. Using the device described in FIG. 3 there are produced, for example, about 50 particles per cm$^3$. Evaporation of the liquid solvent from the solvent-solute droplets takes place rather rapidly at all but very high solute concentrations with about 100–200 ms being sufficient.

After any static charge in the droplets has been neutralized and the droplets dried to form residue particles, the diameter d of the residue particles is then determined. The diameter of the residue particle determines the best choice of the device to be used.

Excellent results have been obtained using devices employing light scattering particle spectrometers for measurements of the diameter d of the residue particle especially when the residue particle has a diameter in the range of 0.1 um to 12 um. An example of a preferred device is illustrated in FIG. 1 of the drawings with a schematic of a general type of this device shown in FIG. 2. The device which is preferred is a light scattering particle spectrometer available from Particle Measuring Systems, Inc. Model LAS-X or LAS-250X.

It should be noted that the laser light scattering spectrometer measures an "optically equivalent sphere" diameter for particles which depend on shape and refractive index of particles. Particles such as NaCl crystals which are not perfectly round but are otherwise sphere-like and in the size range less than 1 um do not generally result in a source of systematic errors. The size differential results in a slight broadening of the pulse distribution which would not be noticeably within the laser light scattering spectrometer resolution.

Saline water droplets evaporate to form a dry solid particle whose volume size is constant and independent of humidity when the relative humidity is less than about 40%-50%. The particles will begin to grow by absorbing water (deliquescence) at higher relative humidities. As mentioned previously, the solid crystals of NaCl are cubes with rounded corners.

Other inorganic particles in very low impurity concentrations are often spherelike but with a polycrystalline and fissured surface appearance as shown by electron micrograph.

By contrast, organic impurities and organic solvents can display a viscous oily nature. The residue droplets thus formed are spherical in shape with a vapor pressure significantly below that of the solvent. The resulting residue droplet is stable enough for analysis by various on-line size analysis techniques. When subjected to heat above ambient temperature, these droplets will evaporate to provide a means of determining whether the impurity is organic or inorganic in nature.

Relative to the above described apparatus for measuring the diameter D of the liquid droplet and the diameter d of the residue particle, the combination of the vibrating orifice generator together with the laser light scattering spectrometer is preferred for measuring impurities in most liquids. One reason is because the resolution and linearity of the light scattering spectrometer is best in a size range of less than 0.7 um. Using a droplet diameter size of 40 um with the laser light scattering spectrometer covering a residue particle diameter size range of 0.5 um to 3 um, an impurity concentration of 0.1 ppm-v to 125 ppm-v can be detected.

For residue particles having a diameter above about 0.5 um, an aerodynamic particle sizer such as an APS 22 available from TSI, Incorporated, can be used.

If the residue particles have a diameter below about 0.1 um to about 0.01 um, an electrostatic classifier as shown in FIG. 4 can be used for size classification in conjunction with a particle detector such as a condensation nuclei counter. A preferred electrostatic classifier is available from TSI, Inc. and a preferred particle detecter is a condensation nuclei counter, Model 3020 manufactured by TSI, Inc..

After the diameter D of the droplet and the diameter d of the residue particle have been determined, the amount of impurities contained in the original liquid expressed as the concentration by volume, $C_v$, is determined from the equation:

$$C_v = (d/D)^3$$

The following example is given for purposes of illustrating the invention and is not intended to constitute a limitation thereof.

EXAMPLE 1

Water and isopropyl alcohol were measured separately for impurity levels within the range of about 0.2 ppm to about 100 ppm taking measurements at 3 to 4 concentration levels for each liquid.

The water used was commercially available bottled DI water having an initial residue level of 0.16 ppmv as given by the invention method described below. As measured by the "residue after evaporation" method the residue level was 0.41 ppmw. Sodium chloride was dissolved in the water to provide impurity levels of 2 ppmw and above.

The isopropyl alcohol used was HPLC grade labeled at less than 2 ppm by the "residue after evaporation" method. Prior to heating of the residue, the measured impurity content was 0.8 ppmv and 0.6 ppmw respectively. After heating, all the residue evaporated. Impurity levels greater than 2 ppm were prepared by mixing the isopropyl alcohol with leachate from neoprene gasket material to provide impurity levels of between about 5 ppm and 100 ppm.

The devices used in measuring the impurities included a vibrating orifice generator substantially as shown in FIG. 3 and a laser light scattering spectrometer substantially as shown in FIG. 1. The vibrating orifice generator used was Model 3450 of TSI, Incorporated. A 20 um orifice was used and the liquid feed rate Q ranged from 0.153 cm³/min to 0.077 cm³/min. The orifice was vibrated at a frequency in the range of 40 kHz-150 kHz. The droplets were introduced into a turbulent flow of ultrafiltered air. A droplet diameter size of 44 um was used for measurements for isopropyl alcohol and a droplet diameter size of 42 um and 23 um for the water measurements.

The residue particle diameter was measured using a laser light scattering spectrometer LAS-250X available from Particle Measuring Systems, Incorporated.

The syringes used included a borosilicate syringe with a Teflon plunger for isopropyl alcohol measurements, and a disposable polypropylene syringe with a neoprene plunger for water measurements. Water or isopropyl alcohol was used to fill the syringe followed by dispensing and atomizing small amounts of the liquid for a droplet size measurement at intervals of 20 minutes or one hour.

For comparative purposes only and not in accordance with the invention, a simultaneous measurement was determined gravimetrically at each concentration using the "residue after evaporation" method. In the case where organic residues were present, the measurements were made before and after heating to 105° C.

The "residue after evaporation" procedure followed was substantially as outlined by ASTM (American Society for Testing Materials) and SEMI (Semiconductor Materials Institute). Basically, each sample was evaporated at a temperature sufficient to maintain low evaporation rates. When water was measured for impurities, the dish was inerted with a coating that had been tested for constant weight over the range of operating temperatures. Evaporation was carried out under Class 100 clean room conditions. The volume of the fluid tested ranged from about 30 cm³ to about 1000 cm³, the exact volume depending upon the levels of impurities present. A microbalance or semimicrobalance was used to determine weights, which choice was governed by the tare weight of the dish.

In order to further provide data for correlation between the invention method and standard methods, certain runs were selected for single particle analysis of the residue particles. In this instance, the measurements were made by SEM and EDS. In the instances where "soft" organic spheres were present, electrostatic precipitation was used to obtain the particle samples. In other instances where solid inorganic particles were present, impaction was used to provide the particle samples.

The results of the measurement of impurities are tabulated in Tables I and II below:

TABLE I

RESIDUE LEVEL MEASUREMENTS FOR ISOPROPYL ALCOHOL
(Error brackets are estimates of random errors).

| Droplet diameter [um] | DROPLET SPRAY METHOD | | BULK EVAPORATION (a) | |
|---|---|---|---|---|
| | Residue Particle Size [um] | Concentration [ppmv] | before heating [ppmw] | Residue After Evaporation [ppmw] |
| 44 | 0.42 ± 0.02 | 0.85 ± 0.15 | 0.6 ± 0.2 | << |
| 44 | 0.95 ± 0.05 | 10 ± 2 | 9.5 ± 2 | << |
| 44 | 1.15 ± 0.1 | 18 ± 5 | 19 ± 2 | << |
| 44 | 2.1 ± 0.2 | 110 ± 30 | 95 ± 5 | << |

(a) Detection limit 0.1 ppmw

TABLE II

RESIDUE LEVEL MEASUREMENTS FOR WATER
(Error brackets are estimates, except for water at 0.41 ppmw where bracket for Res. after Evap. is standard deviation of several runs. Solutions at the 2 and 20 ppmw levels were made with NaCl.)

| Droplet diameter [um] | DROPLET SPRAY METHOD | | BULK EVAPORATION (a) | |
|---|---|---|---|---|
| | Residue Particle Size [um] | Volume Concentration [ppmv] | Residue After Evaporation [ppmw] | Calculated (c) Volume Conc. [ppmv] |
| 42 | 0.23 ± 0.01 | 0.16 ± 0.02 | 0.41 ± 0.1 | (0.19) |
| 23 | 0.13 ± 0.01 | 0.19 ± 0.02 | (b) | |
| 42 | 0.43 ± 0.03 | 1.0 ± 0.2 | 1.9 ± 0.2 | 0.9 |
| 42 | 1.05 ± 0.1 | 15 ± 5 | 21.9 ± 2 | 10 |
| 23 | 0.47 ± 0.04 | 8.5 ± 2 | 21.5 ± 2 | 9.9 |

(a) Detection limit ca. 0.1 ppmw
(b) Same bottle as line above after 8 weeks
(c) Assuming NaCl density of 2.16 g/cm$^3$ The results of Tables I and II show that very high resolution and accuracy can be obtained by the invention method at very low impurity levels. By comparison, the residue or bulk evaporation technique has a detection limit of about 0.1 ppmw. Table II shows that at higher concentrations of impurities there is good agreement between the results except in the case where the residue particle diameter size was 1.05±0.1 um and the droplet diameter size was 42 um. At the same impurity concentration, using a droplet diameter size of 23 um instead of 42 um, good agreement between the two methods was obtained, as shown in the last example of Table II.

Table I shows an uncertainty of ±30 for the measurement of isopropyl alcohol containing 110 ppmv concentration of impurities. This is due to the fact that the droplet diameter size of 44 um produces a residue particle which is too large to provide accurate measurement with the laser light scattering spectrometer. However, this can be overcome by using a smaller droplet diameter size initially. This would then provide a particle size which is within the scope of the laser light scattering spectrometer.

An electron micrograph of water residue particles at the 0.16 ppmv level was made which showed a geometric diameter of 0.22 um. It can be seen from Table II that a water impurity level of 0.16 ppmv shows a residue particle size diameter of 0.23±0.01 um. This also demonstrates the reliability of the invention method.

Tests were conducted, each of which had a duration of one day, in order to determine the contribution of possible impurities by the syringe material. The results of the tests showed that for the isopropyl alcohol, the borosilicate glass syringe with a Teflon plunger showed no detectable fluctuation or drift of the results over time.

However, when the isopropyl alcohol was used with a disposable polypropylene syringe with a neoprene plunger, it was found that impurity levels rose more than 200 fold during the time of the run.

Relative to the water testing over time at a given impurity concentration, the use of a borosilicate glass syringe with the Teflon plunger showed some detectable signs of leaching into the water. An initial level of 0.16 ppm rose to about 0.2 ppm within an hour's period. Using the polypropylene syringe with a neoprene plunger, and after an extended rinse with pure water, no detectable signs of leaching into the water was found until a period of twenty hours had elapsed. After this time there was shown an increase of from 0.16 ppm to 0.18 ppm. In the above tests no heating was used.

The method described herein provides for the rapid measurement of impurities in liquids especially at very low concentrations. By dispersing a droplet of the liquid to be measured, determining its diameter D, evaporating the droplet to leave a residue particle having a diameter d which is measured enables the determination of the concentration by volume $C_v$ in the original liquid according to the equation:

$$C_v = (d/D)^3$$

The method is rapid, each test being capable of completion in less than 5 minutes. In addition, the method is reliably accurate as demonstrated by the results presented in Tables I and II, and inexpensive with regard to the relatively small amounts of the liquid which are required.

Various changes and modifications in the process herein described are contemplated which will occur to those skilled in the art, and can be resorted to without departing from the spirit and scope of the invention as embraced by the appended claims.

We claim:

1. A method for the rapid measurement of the concentration by volume of sub-ppm levels of dissolved impurities in a liquid comprising:

providing a liquid containing dissolved impurities;
dispersing said liquid in a gas stream to generate uniform droplets of precisely known diameter D;
evaporating said droplets while they are carried in said gas stream so that each droplet leaves a residue particle having a diameter d;
measuring the diameter d of the residue particles; and
calculating the concentration by volume, $C_v$, of the dissolved impurities in the liquid according to the equation:

$$C_v = (d/D)^3.$$

2. The method as claimed in claim 1 wherein:
the diameter D of said droplets is in the range of about 20 um to about 50 um.

3. The method as claimed in claim 1 wherein:
any static charges on the droplets and residue particles are neutralized before measuring the diameter d of the residue particles and wherein said liquid is dispersed in said gas stream using a monodisperse droplet generator wherein a jet of said liquid fed by a syringe pump is broken up in a controlled manner into highly uniform droplets of precisely known diameter D by a piezoelectric vibrating orifice which vibrates at a selectable frequency and said droplets are introduced into a turbulent gas stream of said gas, which gas is substantially non-reactive with the liquid or dissolved impurities to disperse and rapidly dry said droplets.

4. The method as claimed in claims 1 or 3 wherein:
the diameter D of said droplets is (one) in the range of about 1 um to about 200 um.

5. The method as claimed in claim 1 or 3 wherein the diameter d of said residue particles is measured with an aerodynamic particle sizer.

6. The method as claimed in claim 3 wherein:
said gas stream is filtered prior to its passage through said monodisperse droplet generator.

7. The method as claimed in claim 1 or 3 wherein:
the diameter d of said residue particles is measured using an electrostatic classifier and a particle detector.

8. The method as claimed in claim 7 wherein said particle detector is a condensation nuclei counter.

9. The method as claimed in claim 3 wherein:
any static charge on said droplets and said residue particles are neutralized electrically by a krypton-85 radioactive neutralizer to reduce the level of static charge on said droplets and said residue particles to near Boltzmann charge equilibrium.

10. The method as claimed in claim 9 further comprising:
periodically heating said gas stream carrying said residue particles to cause evaporation of dissolved organic impurities in said residue particles to enable a determination of whether organic or inorganic dissolved impurities are present in said liquid by comparing the diameter d of said particles before heating with the diameter d of said particles after heating.

11. The method as claimed in claim 3 or 9 wherein:
the diameter d of said residue particles is measured using a light scattering spectrometer.

* * * * *